US011361868B2

(12) United States Patent
Porter et al.

(10) Patent No.: US 11,361,868 B2
(45) Date of Patent: Jun. 14, 2022

(54) ABNORMAL TISSUE DETECTION VIA MODAL UPSTREAM DATA FUSION

(71) Applicant: The Johns Hopkins University, Baltimore, MD (US)

(72) Inventors: David W. Porter, Centerville, MD (US); William C. Walton, Severn, MD (US); Keith S. Peyton, Annandale, VA (US); Susan C. Harvey, Reisterstown, MD (US); Benjamin M W Tsui, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 973 days.

(21) Appl. No.: 16/103,987

(22) Filed: Aug. 16, 2018

(65) Prior Publication Data

US 2019/0057778 A1 Feb. 21, 2019

Related U.S. Application Data

(60) Provisional application No. 62/546,123, filed on Aug. 16, 2017.

(51) Int. Cl.
*G16H 50/50* (2018.01)
*G16H 30/40* (2018.01)
*G16H 50/30* (2018.01)

(52) U.S. Cl.
CPC ............. *G16H 50/50* (2018.01); *G16H 30/40* (2018.01); *G16H 50/30* (2018.01)

(58) Field of Classification Search
CPC ......... G16H 50/50; G16H 50/30; G16H 30/40
See application file for complete search history.

(56) References Cited

U.S. PATENT DOCUMENTS 11,176,676 B2 * 11/2021 Rothrock ................ G06T 7/194
2010/0067768 A1 * 3/2010 Ionasec ..................... G06T 7/35
382/128

(Continued)

OTHER PUBLICATIONS

Teare P. et al., "Malignancy Detection on Mammography Using Dual Deep Convolutional Neural Networks and Genetically Discovered False Color Input Enhancement," Journal of digital imaging, Aug. 2017, 30(4):499-505.

(Continued)

*Primary Examiner* — Rashawn N Tillery
(74) *Attorney, Agent, or Firm* — Todd R. Farnsworth

(57) ABSTRACT

A method for characterizing and locating abnormal tissue in an area of interest in a body is provided. The method may include receiving first and second modality examination data including a plurality of first and second modality examination data segments of the area of interest and determining, by evaluating each first and second modality examination data segment, a set of modality detection candidates based on the first and second modality examination data and a first and second modality feature likelihood model. The method may also include generating a modal or multi-modal correspondence anatomic model of the area of interest by registering the plurality of first and second modality examination data segments, determining one or more modal abnormal tissue detections by fusing the set of modality detection candidates using the modal or multimodal correspondence anatomic model, and providing a modal diagnosis confidence score and a modal anatomic location based on the one or more modal abnormal tissue detections.

20 Claims, 8 Drawing Sheets

(56) References Cited

U.S. PATENT DOCUMENTS

| | | | |
|---|---|---|---|
| 2017/0270666 A1* | 9/2017 | Barnes | G06T 7/12 |
| 2018/0322643 A1* | 11/2018 | Piper | G06T 7/337 |
| 2020/0258235 A1* | 8/2020 | Lu | G16H 50/30 |
| 2021/0133954 A1* | 5/2021 | Melamed | G06K 9/6271 |
| 2021/0225511 A1* | 7/2021 | Kiraly | G06V 10/40 |
| 2022/0036555 A1* | 2/2022 | Auerbach | A61B 8/12 |

OTHER PUBLICATIONS

Li, H. et al., "Non-rigid image registration using fully convolutional networks with deep self-supervision," arXiv preprint arXiv:1709.00799 (2017).

Behrenbruch, C. P. et al., "MRI-mammography 2D/3D data fusion for breast pathology assessment," In International Conference on Medical Image Computing and Computer-Assisted Intervention, pp. 307-316, Springer, Berlin, Heidelberg, 2000.

Bierman, G. J. et al., "Maximum likelihood estimation using square root information filters," IEEE Transactions on Automatic Control, 35(12):1293-1298 (1990).

Trister, A. D. et al., "Will machine learning tip the balance in breast cancer screening?," JAMA Oncology, Nov. 2017, 3(11):1463-1464.

Shi, X. et al., "Detection and classification of masses in breast ultrasound images," Digital Signal Processing, May 2010, 20(3):824-836.

Amit, G. et al., "Classification of breast MRI lesions using small-size training sets: comparison of deep learning approaches," Proc. SPIE 10134, Medical Imaging 2017: Computer-Aided Diagnosis, 101341H (Mar. 3, 2017).

Arevalo, J. et al., "Representation learning for mammography mass lesion classification with convolutional neural networks," Computer methods and programs in biomedicine, 127 (2016) 248-257.

Newman, A. J. et al., "Upstream data fusion: History, technical overview, and applications to critical challenges." Johns Hopkins APL Technical Digest, vol. 31, No. 3, (2013), pp. 215-233.

Miao, S. et al., "A CNN regression approach for real-time 2D/3D registration," IEEE transactions on medical imaging, vol. 35, No. 5 (2016), pp. 1352-1363.

Brock, K. K. et al., "Accuracy of finite element model-based multi-organ deformable image registration," Med. Phys. 32 (6), Jun. 2005, pp. 1647-1659.

Athiwaratkun, B. et al., "Feature Representation in Convolutional Neural Networks," arXiv preprint arXiv:1507.02313 (2015).

Geras K. J. et al., "High-resolution breast cancer screening with multi-view deep convolutional neural networks," arXiv preprint arXiv:1703.07047 (2017).

Porter, D. W. "Data Fusion Modeling for Groundwater Systems using Generalized Kalman Filtering," Book: Stability and Control of Dynamical Systems with Applications, Birkhauser, Boston, 2003, pp. 331-354.

Froeling, V. et al. "Correlation of contrast agent kinetics between iodinated contrast-enhanced spectral tomosynthesis and gadolinium-enhanced MRI of breast lesions," Eur Radiol (2013) 23:1528-1536.

Carl E. Raven Advanced Imaging Laboratories, "Computer-aided diagnosis: Breast imaging," available at: https://web.archive.org/web/20160524160639/http://deckard.mc.duke.edu/breastcad.html.

Van Ginneken, B. et al. "Computer-aided diagnosis: how to move from the laboratory to the clinic." Radiology, vol. 261, No. 3 (2011), pp. 719-732.

Mahoney, M. C. et al., "False positive marks on unsuspicious screening mammography with computer-aided detection," J Digit Imaging (2011) 24:772-777.

Mingyang, L. et al., "Modeling putative therapeutic implications of exosome exchange between tumor and immune cells," PNAS Sep. 22, 2014 111 (40) E4165-E4174.

Levy, L. J. et al., "Large-Scale System Performance Prediction with Confidence from Limited Field Testing Using Parameter Identification," Johns Hopkins APL Technical Digest, vol. 13, No. 2 (1992), p. 300-308.

Singh, N. et al., "Topological Descriptors of Histology Images." In: Wu G., Zhang D., Zhou L. (eds) Machine Learning in Medical Imaging. MLMI 2014. Lecture Notes in Computer Science, vol. 8679. Springer, Cham.

Reid, Donald B., "An Algorithm for Tracking Multiple Targets," IEEE Transactions on Automatic Control, vol. AC-24, No. 6, Dec. 1979.

Wigren, Torbjom, "Target-type probability combining algorithms for multisensor tracking," Proc. SPIE 4380, Signal Processing, Sensor Fusion, and Target Recognition X, Aug. 2001.

Bar-Shalom, Yaakov et al., "Tracking with Classification-Aided Multiframe Data Association," IEEE Transactions on Aerospace and Electronic Systems, vol. 41, No. 3, Jul. 2005.

Porter, D. W., "Quantitative Data Fusion: A Distributed/Parallel Approach to Surveillance, Tracking, and Navigation Using Information Filtering," Proc. Fifth Joint Service Data Fusion Symposium, JHU/APL (Oct. 1991).

* cited by examiner

ABNORMAL TISSUE DETECTION VIA MODAL UPSTREAM DATA FUSION

CROSS-REFERENCE TO RELATED APPLICATIONS

This application claims the benefit of U.S. Provisional Application No. 62/546,123 filed on Aug. 16, 2017, the entire contents of which are hereby incorporated herein by reference.

TECHNICAL FIELD

Example embodiments generally relate to medical technology and, in particular, relate to apparatuses, systems, and methods for computer-aided detection of biologic abnormalities.

BACKGROUND

Breast cancer is currently the most common cancer for women globally. Over 1.7 million women will be diagnosed with breast cancer and over ½ million women have died due to the disease in 2017 alone. Early detection of breast cancer is known to dramatically improve mortality, with mortality rates being decreased between 20 and 40% depending on the age and frequency of screening mammography. Yet despite these gains, there are severe limitations in the accuracy of conventional breast cancer detection related to the modalities currently available and human limitations in identifying cancers on these modalities. Additionally, the overlap of the appearance of normal and abnormal tissue leads to low specificity and high false positives which are costly for to the health care system and stressful for patients.

X-ray and other imaging technologies operate to assist radiologists with diagnosing a multitude of medical conditions including breast cancer by visually identifying lesions and other tissue abnormalities. These imaging technologies typically capture many images of an area of interest for viewing by a radiologist. In this regard, imaging systems can be employed to capture image data from various viewpoints (e.g., two-dimensional cross-section images of the area of interest, often taken at differing orientations and angles). The raw captured image data is often then processed to transform the data into an image for rendering on a monitor to be viewed by the radiologist. Possibly hundreds or even thousands of views of an area of interest may be rendered and the radiologist may be required to move through those rendered images to identify suspect features that may be indicative of, for example, a cancerous tumor. With that many images to view, the radiologist may, for example, inadvertently miss a potential cancerous tumor.

While imaging technologies continue to advance to provide more contrast and less noise within these image renderings, read times are still long and the frequency of false positives is still too high. Because patients are subjected to the uncomfortable procedures, such as surgical biopsies and the like due to false positives, improvements to reduce read times and decrease the rate of false positive diagnoses would be valuable.

BRIEF SUMMARY OF SOME EXAMPLES

According to some example embodiments, a method for characterizing and locating abnormal tissue in an area of interest in a body is provided. The method may comprise receiving first modality examination data of the area of interest captured by a medical imaging device. The first modality examination data may comprise a plurality of first modality examination data segments, and each first modality examination data segment may be associated with a portion of the area of interest or a first modality sensor field of view into the area of interest. The method may also comprise using a data conditioner computing machine to determine, by evaluating each first modality examination data segment, a set of first modality detection candidates based on the first modality examination data and a first modality feature likelihood model. In this regard, each first modality detection candidate may comprise a first modality likelihood score and a first modality relative location. The method may also comprise generating, by a data fusion machine, a modal correspondence anatomic model of the area of interest by registering the plurality of first modality examination data segments, determining, by a data fusion machine, one or more modal abnormal tissue detections by fusing the set of first modality detection candidates using the modal correspondence anatomic model, and providing, by a data fusion machine, a modal diagnosis confidence score and a modal anatomic location based on the one or more modal abnormal tissue detections. From ingestion of the raw modality examination data to producing abnormal tissue detections, the method is completely automated in computing machines with no human intervention.

According to some example embodiments, a system for characterizing and locating abnormal tissue in an area of interest in a body is provided. The system may comprise processing circuitry configured to receive first modality examination data of the area of interest. The first modality examination data may comprise a plurality of first modality examination data segments, and each first modality examination data segment may be associated with a portion of the area of interest or a first modality sensor field of view into the area of interest. The processing circuitry may be further configured to determine, by evaluating each first modality examination data segment, a set of first modality detection candidates based on the first modality examination data and a first modality feature likelihood model. Each first modality detection candidate may comprise a first modality likelihood score and a first modality relative location. The processing circuitry may be further configured to generate a modal correspondence anatomic model of the area of interest by registering the plurality of first modality examination data segments, determine one or more modal abnormal tissue detections by fusing the set of first modality detection candidates using the modal correspondence anatomic model, and provide a modal diagnosis confidence score and a modal anatomic location based on the one or more modal abnormal tissue detections.

BRIEF DESCRIPTION OF THE SEVERAL VIEWS OF THE DRAWING(S)

Having thus described some example embodiments in general terms, reference will now be made to the accompanying drawings, which are not necessarily drawn to scale, and wherein:

DETAILED DESCRIPTION

Figure 1:
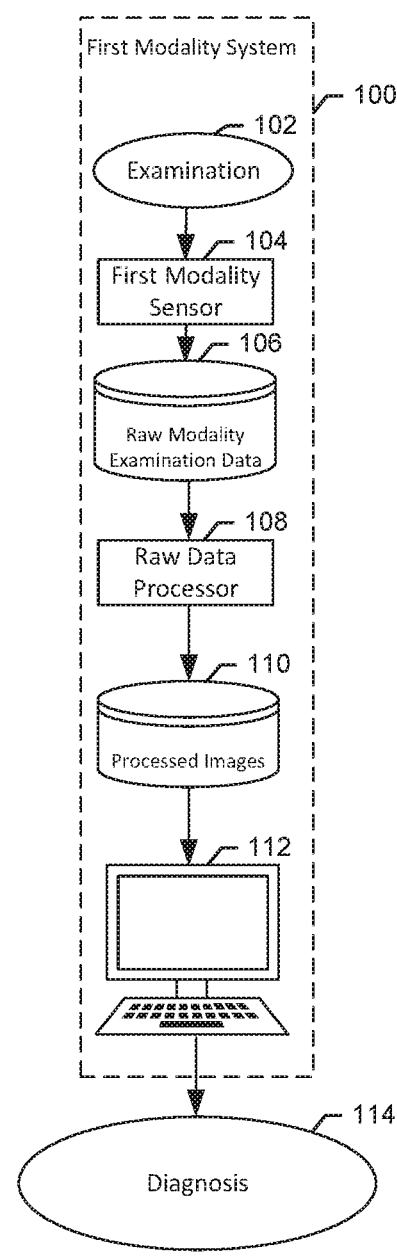
FIG. 1 illustrates a modality system for assisting with diagnosing abnormal tissue.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. As used herein, operable coupling should be understood to relate to direct or indirect connection that, in either case, enables functional interconnection of components that are operably coupled to each other.

Example methods, apparatuses, and systems are described herein that operate to characterize and locate abnormal tissue (e.g., malignant tumors or lesions) within an area of interest in a body (e.g., a human body). To do so, according to some example embodiments, an upstream data fusion (UDF) approach may be utilized that combines data from single or multiple data capturing modalities to produce new information and inferences that provide, for example, an anatomic location of abnormal tissue in the area of interest and a quantitative confidence score with respect to the malignancy of the located abnormal tissue. Example modalities include medical imaging devices that may produce data for use with such a UDF approach which may include, but are not limited to, ultrasound, positron emission tomography (PET), computed tomography (CT), x-rays, magnetic resonance imaging (MRI), single-photon emission computed tomography (SPECT), or the like. Within a single modality, data may be generated that is representative of portions or cross-sectional slices of the area of interest in the body. Such data segments may be evaluated separately to determine detection candidates that are associated with a likelihood score and a relative location. These likelihood scores and locations may be subsequently associated and fused, as further described herein, to generate abnormal tissue detections that include a diagnosis or malignancy confidence score and an anatomic location.

Accordingly, the example embodiments described herein improve upon the prior art technology in the radiology space to, for example, reduce read times and reduce false positives. In this regard, conventional technologies that are used for cancer detection are generally at best similar in performance to expert radiologists. Currently, the data processing that is performed in the radiology space is mainly dedicated to rendering hundreds or even thousands of images and providing a user interface for radiologists to move through the rendered images to make a diagnosis. Due to the overwhelming amounts of image data but still relatively poor performance outcomes, there exists a gap between what is desired to assist radiologists and what has been achieved in terms of early detection, minimization of unnecessary biopsies, and reduction of excessive false positives. As such, a technical problem exists in the radiology space in that substantial quantities of data from, for example, x-ray, MRI, and other modalities exist, but the ability to transform this substantial amount of data into usable information has been limited. The current state of the art is unable to accurately combine multiple sources of medical imaging data to accurately detect abnormalities in an area of interest.

According to various example embodiments, systems described herein that can integrate UDF into the data analysis process offer a technical solution that transforms the unwieldy amount of available data into helpful, concise information that can be leveraged to obtain improved results with respect to reduced read times and reduced false positives. In this regard, according to some example embodiments, machine learning can be used to produce feature likelihood models that may be applied to determine detection candidates for individual sensing modalities that would conventionally have high detection rates and high false positive rates. Further, data fusion, e.g., via UDF, can be employed to combine detection candidates and associated data, within or between modalities, to generate modal abnormal tissue detections with modal diagnosis confidence scores and associated locations that can be leveraged to reduce radiologist read times and the false positive rate. Additionally, upstream data that is raw data or at least closer to raw data and may be impossible or difficult for operators to visualize or properly utilize, such as ultrasound waveform data, may be used for the fusion method, thereby recovering information to obtain improved results that would otherwise be lost using conventional methods.

In this regard, for example, data results for specifically breast cancer detection that fuse Digital Breast Tomosynthesis (DBT) and MRI indicate that employing UDF as described herein can reduce radiologist read time and reduce false positives. As such, according to some example embodiments, a UDF machine learning system may be implemented to realize at least these benefits by combining, for example, data from a range of modalities such as DBT, automated breast ultrasound (ABUS), MRI, PET, and SPECT. Further, demographic and other non-modality data may also be combined to further improve results. In addition, data may be combined from examinations that are nearly coincident in time, for example within days of each other, or from examinations that are separated in time, possibly for months, to perform diagnoses such as change detection in tissue abnormalities.

According to some example embodiments, data fusion via, for example, UDF, as described herein, may be performed by a data fusion machine, such as specially configured data processing circuitry, configured to repeatedly consider differing instances of input data (e.g., modal image data) and automate bringing those instances together (e.g., fusing) to facilitate for accurate cancer detection (or other abnormalities). To do so, raw data or near raw data, which may be referred to as upstream data, from the one or more modalities may be used, rather than using processed downstream data that has already lost valuable information. By using upstream data, particularly when combining data from different modalities, valuable information that was previously buried in noise or impossible to visualize may be recovered and utilized in the detection process. For example, three dimensional mammographic images can be formed from a sequence of two dimensional images taken at different angles, and the sequence of upstream images includes critical useful mathematical information. Further, ABUS upstream waveform data can also include important information that UDF can utilize for improved results.

FIG. 1 illustrates a conventional single modality system, that is first modality system 100, for diagnosing malignant tissue. In this regard, the first modality system 100 may leverage a first modality sensor 104 (e.g., an x-ray machine, an MRI machine, or the like) during a patient examination 102 to generate raw modality examination data 106. The raw modality examination data 106 may, for example, be data that is output directly from the first modality sensor 104. In this regard, with reference to FIGS. 2A through 2C, depending on the type of modality and the associated sensor, the raw modality examination data 106 may be considered a collection of data segments that describe a particular portion or view point of the area of interest.

Figure 2A:
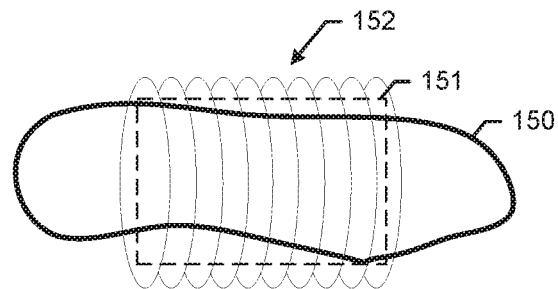
FIGS. 2A-2C illustrate example techniques for generating data segments in accordance with different modalities according to some example embodiments.
Figure 2B:
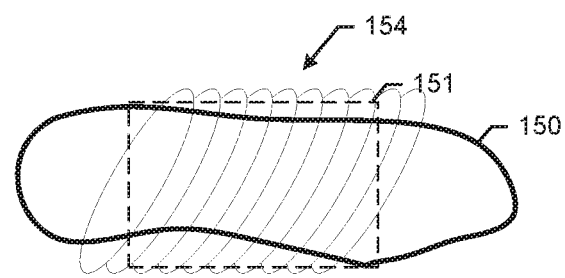

With reference to FIG. 2A, the associated modality may be one that, via the first modality sensor 104, generates raw modality examination data 106 that can be segmented such that each segment is associated with one of a plurality of two-dimensional cross-sectional slices 152. For example, the first modality may correspond to an MRI. In this regard, FIG. 2A illustrates a body 150 having an area of interest 151. The first modality sensor 104 may be configured to capture data that can be used to render a plurality of images of the area of interest 151 and correspond to respective ones of the slices 152. The data segment of the raw modality examination data 106 associated with each slice 152 may include data representative of the features that may be present within the body 150 at the location of the cross-sectional view. With reference to FIG. 2B, the same or a similar sensor 104 may reoriented or otherwise moved to generate additional raw data associated with a plurality of two-dimensional cross-sectional slices 154 of the area of interest 151 of the body 150. In this regard, the data segments of this additional raw data may be associated with the slices 154 which are oriented at an angle relative to the slices 152. As such, data segments within the raw data may overlap with respect to a particular area or volume. In this regard, the data associated with slices 152 and the data associated with slices 154 may, in combination, be raw modality examination data 106.

Figure 2C:
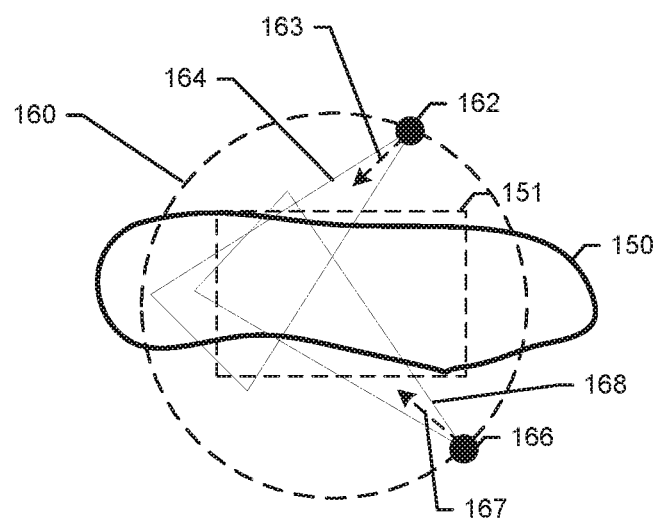

Further, with reference to FIG. 2C, the associated modality may be one that, via the first modality sensor 104, generates raw modality examination data 106 that can be segmented such that each segment is based on a field of view of the sensor 104 into the area of interest 151 into the body 150. In this regard, the field of view of the sensor 104 may be defined by a location of the sensor 104 and a sensor direction. Such a sensor 104 may be, for example, an ultrasound sensor. In this regard, the sensor 104 may move about the body 150, and the area of interest 151, for example, along a path 160. As the sensor 104 moves, the sensor 104 may capture raw modality examination data 106. For example, a first segment of the raw modality examination data 106 may be associated with the field of view 164 as defined by sensor location 162 and direction 163. Similarly, a second segment of raw modality examination data 106 may be associated with the field of view 168 as defined by sensor location 166 and direction 167.

While the raw modality examination data 106 may take a number of different forms based on the particular modality, the raw modality examination data 106 may be processed after being captured by the sensor 104. In this regard, either internal to the sensor 104 or remote from the sensor 104, the raw modality examination data 106 may be processed, by raw data processor 108. Raw data processor 108 may operate to convert the raw modality examination data 106 into processed images 110. In the conversion process, detailed information that is present in the raw modality examination data 106 may be lost in order to generate the processed images 110 for rendering. Nonetheless, the processed images may be rendered on a monitor 112 for viewing by a radiologist. Upon review of the requisite number of images, the radiologist may make a diagnosis at 114 indicating whether or not the processed images 110 reveal, for example, a candidate lesion that may need to be further investigated via a biopsy or the like.

Figure 3:
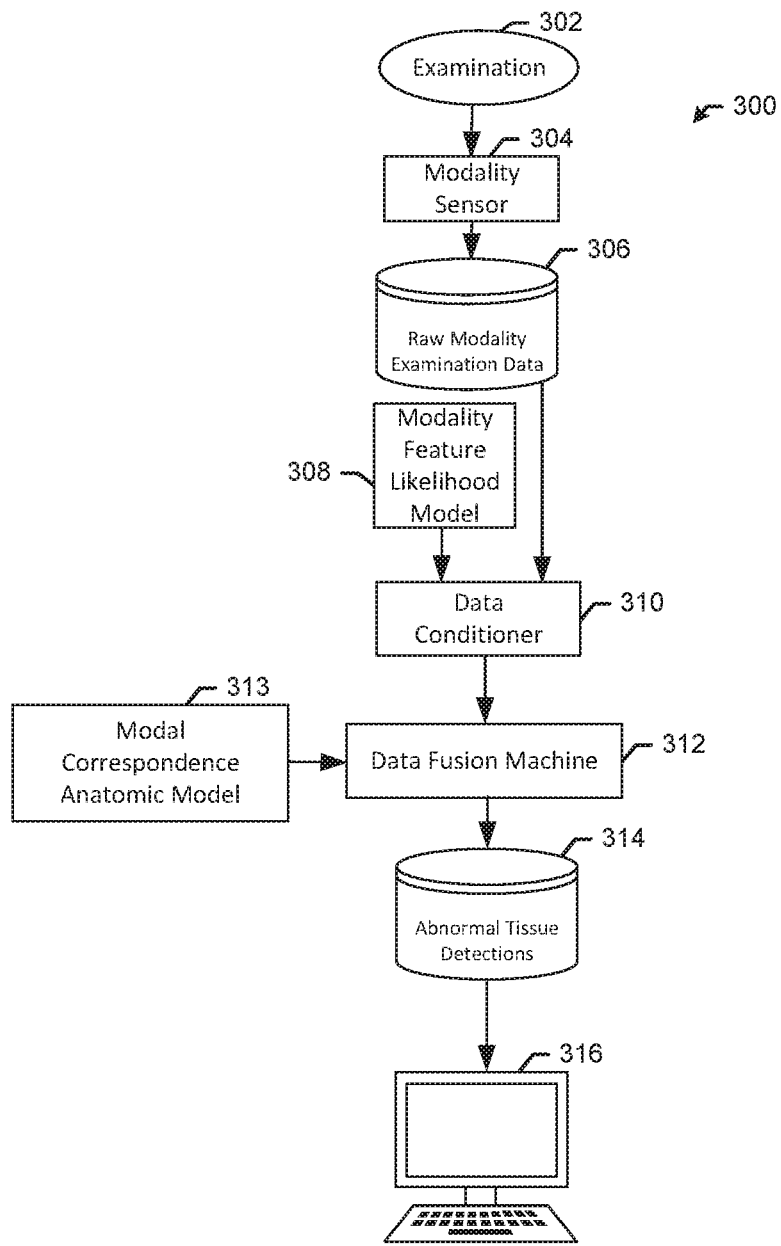
FIG. 3 illustrates an example system for generating abnormal tissue detections based on a single modality according to some example embodiments.

According to some example embodiments, FIG. 3 illustrates a system 300 that can leverage the capturing of raw data pursuant to a particular modality and apply a UDF approach to generate abnormal tissue detections in an automatic fashion. In this regard, the system 300 may operate with respect to a particular modality in the context of one or more examinations 302 of a patient. Based on the modality, a sensor 304 may operate to capture raw modality examination data 306 in a manner similar to sensor 104. However, according to some example embodiments, the raw modality examination data 306 may be handled differently according to some example embodiments.

In this regard, the raw modality examination data 306 may, according to some example embodiments, be provided to a data conditioner 310. The data conditioner 310 may be a data processing device with processing circuitry (e.g., including a processor, CPU, GPU, FPGA, etc.) configured to determine a set of modality detection candidates based on the raw modality examination data 306. The data conditioner 310 may be physically located at any location that is capable of receiving the raw modality examination data 306. However, according to some example embodiments, the data conditioner 310 may be located relatively close to the sensor 304 to reduce bandwidth requirements associated with transmitting the raw modality examination data 306. In this regard, a reduction in the amount of transmitted data may be realized if the data conditioner 310 is located local to the sensor 304. Additionally, with respect to the reduction of the amount of data being transmitted, according to some example embodiments, the data conditioner 310 or another entity may be configured to filter the raw modality examination data 306 in a manner that merely reduces non-meaningful noise in the raw modality examination data 306.

The data conditioner 310 may be configured to evaluate each modality examination data segment within the raw modality examination data 306. In this regard, each modality examination data segment may be considered in isolation from any other data segment. Data conditioning may be performed in steps where the first step operates on all the data in the segment with a simple fast algorithm (as described below) to eliminate data obviously not of interest, and subsequent steps use more complicated algorithms for refinement that are applied only to data from previous steps to eliminate more data until the candidate detections are obtained. The data conditioner may apply the first step of processing for a segment that is in the form of a slice in a sliding window. The processing may be performed on data in the window where the window slides back and forth across the image advancing a fraction of its width each time it slides so it overlaps some previous windows and the sliding windows cover the entire slice. According to some example embodiments, the data conditioner 310 may be configured to apply, for example, as a first step, detection algorithms such as a Constant False Alarm Rate (CFAR) detection, detection using engineered features such as texture, or detection using features discovered from deep learning. Such methods may be seen, for example, in Teare P. et al, "Malignancy Detection on Mammography Using Dual Deep Convolutional Neural Networks and Genetically Discovered False Color Input Enhancement," Journal of digital imaging, 2017 Aug. 30(4):499-505; and Newman, Andrew J. and Glenn E. Mitzel, "Upstream data fusion: History, technical overview, and applications to critical challenges." Johns Hopkins APL technical digest 31.3 (2013): 215-233, the entire contents of both are hereby incorporated herein by reference. As a result of applying such a detection algorithm to each of the modality examination data segments (e.g., in isolation from other modality examination data segments), a preliminary set of candidate detections may be determined. Within this preliminary set, for example, neighboring candidate detections may be grouped together using segmentation or clustering methods to identify candidate object detections. A subsequent step for the data conditioner 310 may include using a modality feature likelihood model 308 to perform feature discrimination on the preliminary set of candidate detections. The application of the modality feature likelihood model 308, according to some example embodiments, may be performed with a detection threshold that results in determination of a set of modality candidate detections, for example, with a high probability of detection, but also a high false alarm rate. In this regard, according to some example embodiments, the set of modality candidate detections may include candidate detections that are statistically more likely to be associated with a false positive than a true positive when considered in the context of a single data segment. To address this, the data fusion machine 312 may be configured to process the set of modality candidate detections as a group (and not in isolation) across multiple data segments to reduce the false alarm rate as part of the fusion process, which is able to extract valuable information, even from candidate detections that are more likely to be a false positive, due to the holistic approach. For example, there may be several modality detection candidates on a lesion that is not malignant, but, due to noise, a few of the modality feature likelihood scores for malignancy could be high. If the candidate detections that are more likely to be false positives with low scores are removed with feature discrimination, then the remaining higher score candidate detections may generate a false positive abnormal tissue detection. But if the candidate detections that are more likely to be false positives are not removed, then the holistic approach can determine that most of the candidate detections have low scores and the false positive abnormal tissue detection can be avoided. This holistic approach is not seen in the current state of the art.

Additionally, the output of the data conditioner 310 may include modality detection candidates, where each modality detection candidate includes likelihood scores and a relative location for the detection associated with each modality examination data segment. For each candidate detection, the likelihood score may be a vector or set of likelihood values for each candidate object class. In this regard, for example, the candidate object classes may include a malignant lesion class, a benign lesion class, and a random clutter class. The likelihood values may be the probabilities of the measured data in terms of machine learning decision variables (such as provided by a Support Vector Machine (SVM)) given the classes and the likelihood values are obtained from the modality feature likelihood model 308. The likelihood score may be a vector with a separate likelihood value for each class for the data associated with a detection candidate. There may also be classes for different types of malignant lesions and different types of benign lesions for more specific diagnoses when the data can support such diagnoses and associated likelihood values may be determined for these additional classes. In addition, a persistent clutter class may be included for objects that are not lesions, but nonetheless are detected by the data conditioner 310 and persist in different data segments of the same modality or different modalities, such as, for example, detections associated with the breast glandular structure. The relative location, that is a component of a modality detection candidate, may be a pixel location for the centroid of the detected object in, for example, a data segment that is a 2D image slice. The relative location may be accompanied by a statistical location uncertainty for the relative location.

As the data conditioner 310 considers each of the data segments, the data conditioner 310 may collect a set of modality detection candidates. According to some example embodiments, the data conditioner 310 may employ relaxed decision criteria with respect to which modality detection candidates are included in the set. In this regard, candidates having low modality likelihood scores, that is candidates that are unlikely to describe abnormal tissue in the form of a malignant lesion, may nonetheless be included in the set because such low likelihood scores may be useful when combining or fusing with other likelihood scores for the same or nearby locations. The use of low modality likelihood scores allows for an ability to establish locations where data can be fused to help to avoid corruption of true detects.

The data conditioner 310 may be configured to pass the set of modality detection candidates (e.g., via a network) to a data fusion machine 312 to perform UDF and obtain abnormal tissue detections. The data fusion machine 312 may include a processor or processing circuitry specially configured to perform data fusion as described herein to provide modal diagnosis confidence scores and modal anatomic locations based on the one or more modal abnormal tissue detections.

To facilitate performing the data fusion, a modal correspondence anatomic model 313 may be generated by the data fusion machine 312. To generate the modal correspondence anatomic model 313, each of the modality examination data segments may be evaluated as part of a registration process to determine the spatial relationship of the modality examination data segments to each other. The registration process may involve, for example, identifying mutual information amongst the data segments or data segment similarity measures, while accounting for tissue deformation such as breast compression for mammography. In this regard, according to some example embodiments, the data fusion machine 312 may be configured to analyze features within the modality examination data segments to identify registration features and extract matchable characteristics of the registration features to locationally link the modality examination data segments. In this regard, for example, the data fusion machine 312 may be configured to evaluate each of the modality examination data segments to identify registration features within the modality examination data segments that exceed a characteristic threshold and include a matchable characteristic. For example, the characteristic threshold may be an image contrast threshold or a sharpness threshold, and a feature that exceeds such as characteristic threshold may be likely to have, for example, matchable characteristics such as sharp edges. Accordingly, the data fusion machine 312 may be configured to identify, for a selected registration feature, two or more modality examination data segments that include the matchable characteristic (e.g., the particular sharp edges). Upon identifying modality examination data segments that include the matchable characteristic (or a predictable variation of the matchable characteristic based on relative known locational relationships between the modality examination segments), the data fusion machine 312 may generate a location-based linkage between the two or more modality examination data segments associated with the selected registration feature for inclusion in the modal correspondence anatomic model 313. As such, the modal correspondence anatomic model 313 may take the form of, for example, a spline model, finite element elasticity model, or a machine learning spatial transformer network. Due to the inherent 3D nature of much of the modality examination data 306, the registration process may use stacks of slices of examination data as blocks of data to build a correspondence model within and between modalities, as further described with respect to FIG. 5. In this manner, mutual information and similarity measures may be used to register stacks of slices simultaneously. Examples where machine learning is used may be found in Li, Hongming, and Yong Fan, "Non-rigid image registration using fully convolutional networks with deep self-supervision," arXiv preprint arXiv:1709.00799 (2017); and Miao, Shun et al., "A CNN regression approach for real-time 2D/3D registration," IEEE transactions on medical imaging 35.5 (2016): 1352-1363, the entire contents of both are hereby incorporated herein by reference. An example of where a spline approach is used may be found in Behrenbruch, Christian P. et al., "MRI—mammography 2d/3d data fusion for breast pathology assessment," In International Conference on Medical Image Computing and Computer-Assisted Intervention, pp. 307-316, Springer, Berlin, Heidelberg, 2000, the entire contents of which are hereby incorporated herein by reference. An example of a finite element approach may be found in Brock, K. K. et al., "Accuracy of finite element model-based multi-organ deformable image registration," Medical physics 32, No. 6 Part 1 (2005): 1647-1659, the entire contents of which are hereby incorporated herein by reference.

With the modal correspondence anatomic model generated, the data fusion machine 312, may be configured to perform data association on the data segments as part of the data fusion. In this regard, because the data segments may be descriptive of areas or regions that overlap, some modality detection candidates, provided by the data conditioner 310, may refer to a common anatomical object, and thus an association may be made in such instances.

The data fusion machine 312 may receive inputs including the modality detection candidates. Based on the modality detection candidates, the data fusion machine 312 may perform data fusion operations, such as, data association, to produce modal abnormal tissue detections 314. According to some example embodiments, the modal abnormal tissue detections 314 may be determined by the data fusion machine 312 by generating and subsequently pruning a plurality of object association hypotheses. In this regard, as further described below, the data fusion machine 312 may be configured to generate a plurality of object association hypotheses, where each object association hypothesis is associated with one or more modality detection candidates based at least on the first modality relative locations. Further, the data fusion machine 312 may be configured to determine a probability of association for each object association hypothesis, and remove (or prune) one or more object association hypotheses based on the probability of association for the object association hypothesis failing to meet an association threshold (e.g., indicating that the associated modality detection candidates have a low probability of association). Accordingly, based on the resultant set of object association candidates, the data fusion machine 312 may determine the one or more modal abnormal tissue detections 314 based on the remaining object association hypotheses.

Following from the above, data association may operate to associate the modality detection candidates by identifying and selecting multiple object association hypotheses having a high likelihood of being associated to common objects. For each object association in the multiple object association, the formulated hypothesis is that the physical object exists and that the modality detection candidates are associated with the object. According to some example embodiments, the object associations cannot share modality detection candidates because a single detection candidate should not be associated with two different objects. The segment modality detection candidates may be processed sequentially where a new segment (or new segments taken as a batch due to the 3D nature of the examination data and the known relative anatomic locations associated with the data segments) is combined with previous association hypotheses. For example, a first step to process a new segment (or batch of segments) may be to consider all possible associations of each new modality detection candidate with each previous object association. In this regard, a gating process may be performed where associations that are inconsistent in terms of likelihoods (e.g., based on a minimum threshold likelihood of association) and locations (e.g., more than a threshold distance apart) may be removed from consideration. The previous object associations may be referred to as parent associations and the new associations may be referred to as child associations. Additionally, data association may include considering a possibility that each modality detection candidate could be a new object or a false alarm.

A second step, performed by the data fusion machine 312, may be to perform multiple object association hypothesis expansion. To do so, parent hypotheses made up of parent object associations are expanded to form child hypotheses made up of child object associations that were formed earlier (e.g., in the first step). Accordingly, all possible hypotheses may be formed (considering that object associations should not share data), and all the data may be included. Subsequently, hypothesis pruning may be performed to remove hypotheses that are not of interest by removing those with low probability of correct association.

The probabilities of the multiple object hypotheses may be computed using inverse probability based on likelihoods, data conditioner parameters such as probability of detection and false alarm rate, and prior knowledge of object density available from training data. The following equations may be used to calculate the probability P of the multiple object association hypotheses sequentially as new segment data are fused with previous segment data for k−1 segments $Z^{k-1}$ $$P(\Omega_i^k \mid Z^k) = P(\Psi_h, \Omega_g^{k-1} \mid Z(k), Z^{k-1})$$

$$P(\Psi_h, \Omega_g^{k-1} \mid Z(k), Z^{k-1}) =$$

$$\frac{P(Z(k) \mid \Psi_h, \Omega_g^{k-1}, Z^{k-1}) * P(\Psi_h \mid \Omega_g^{k-1}, Z^{k-1}) * P(\Omega_g^{k-1} \mid Z^{k-1})}{P(Z(k) \mid Z^{k-1})}$$

where $\Omega_1^k$=multiple object association hypothesis=$\{\Psi_h, \Omega_g^{k-1}\}$
$\Psi_h$=child data association hypothesis; $\Omega_g^{k-1}$=parent hypotheses through k−1 segments $Z(k) = \{z_1(k), z_2(k), \ldots, z_m(k)\}$ is the set of measurements on the current segment k With reference to the equation above, the term $$P(\Omega_g^{k-1} | Z^{k-1})$$

is the probability of the parent multiple object association hypothesis. The term $$P(\Psi_h | \Omega_g^{k-1}, Z^{k-1})$$

depends only on the data conditioner parameters and object density. The term $$P(Z(k) | \Psi_h, \Omega_g^{k-1}, Z^{k-1})$$

is the conditional likelihood of the new segment modality detection candidates given the child and parent data association hypotheses and given the previous segment modality detection candidates. This likelihood may be computed using the modality detection candidate likelihoods and location data by the following equations:

$$P(Z(k) | \Psi_h, \Omega_g^{k-1}, Z^{k-1}) = \prod_{j=1}^{m_k} p(z_j(k) | \Psi_h, \Omega_g^{k-1}, Z^{k-1})$$

$$p(z_j(k) | \Psi_h, \Omega_g^{k-1}, Z^{k-1}) = $$
$$p(z_{ks,j}(k) | \Psi_h, \Omega_g^{k-1}, Z^{k-1}) * p(z_{fs,j}(k) | \Psi_h, \Omega_g^{k-1}, Z^{k-1})$$

where modality detection candidates within a segment are assumed to be statistically independent and data in location space ($z_{ks}$) and feature space ($z_{fs}$) are statistically independent.

The location space term may then be computed from inverse probability using a Square Root Information Filter (SRIF) that computes an estimate for object location using the modality detection candidate relative locations in the segments and the modal correspondence anatomic model. For the SRIF, the log of the location term $$p(z_{ks,j}(k) | \Psi_h, \Omega_g^{k-1}, Z^{k-1})$$

in the above equations is $$-\frac{1}{2}\left(e_k^t e_k + 2 \frac{\log \det R_{k|k}}{\log \det R_{k|k-1}}\right)$$

as provided in Bierman, G. J., Belzer, M. R., Vandergraft, J. S, and Porter, D. W., "Maximum likelihood estimation using square root information filters," IEEE Transactions on Automatic Control, 35(12):1293-1298 (1990), which is herein incorporated by reference in its entirety. The feature space term may be computed by the following where the association hypothesis notation is suppressed and where the modality detection candidate likelihoods are $P(z_{fs,j}(k)|T_i, Z_{fs}^{k-1})$ for the object classes $T_i$:

$$p(z_{fs,j}(k) | \Psi_h, \Omega_g^{k-1}, Z_{fs}^{k-1}) =$$
$$\begin{cases} p(z_{fs,j}(k) | FT), \text{ for false object} \\ \sum_{i=1}^{N_T} p(z_{fs,j}(k), T_i | Z_{fs}^{k-1}), \text{ for detected object} \end{cases}$$

$$\sum_{i=1}^{N_T} p(z_{fs,j}(k), T_i | Z_{fs}^{k-1}) = \sum_{i=1}^{N_T} p(z_{fs,j}(k) | T_i, Z_{fs}^{k-1}) * P(T_i | Z_{fs}^{k-1})$$

$$P(T_i | Z_{fs}^k) = \frac{P(z_{fs,j}(k) | T_i, Z_{fs}^{k-1}) * P(T_i | Z_{fs}^{k-1})}{P(z_{fs,j}(k) | Z_{fs}^{k-1})}$$

The above assumes a finite number of exhaustive and mutually exclusive discrete object classes. The last equation provides the modal diagnosis confidence score as a classification probability. This provides classification for abnormal tissue detections 314 that have been determined based on a single modality in the context of the system 300, or classification for abnormal tissue detections 596 that have been determined based on multiple modalities in context of the system 500, as further described below. Now the probability of a specific object association can be computed as the sum of all the probabilities of the multiple object association hypotheses that contain the specific object association. Object associations with sufficiently high probability of correct association provide modal abnormal tissue detections 314. Also there may be lower probability object associations that can be considered for detections. It is possible for several object associations to share most of their data and be similar in location but to individually have low probability. However, since these may share data, they cannot be in the same multiple object association hypothesis. As such, the object associations can be grouped and the probability for the group is the sum of the individuals. If the group probability is high and the malignant lesion confidence score is high the group may provide a useful output.

The abnormal tissue detections 314 comprise a modal diagnosis confidence score, modal anatomic location, and data association confidence score. The modal diagnosis confidence score may be quantified by the classification probability ($P(T_i|Z_{fs}^k)$), for example, the probability of malignancy. The modal anatomic location may be provided by the estimate for object location and an associated quantified location uncertainty, for example, location error covariance that may be computed as provided in Bierman, G. J., Belzer, M. R., Vandergraft, J. S, and Porter, D. W., "Maximum likelihood estimation using square root information filters," IEEE Transactions on Automatic Control, 35(12): 1293-1298 (1990), the entire contents of which is herein incorporated by reference. In an embodiment, the data association confidence score is provided by the probability of correct association.

As such, based on the abnormal tissue detection 314, a cancer detection may be determined when the probabilities of correct association and a sufficiently high modal diagnosis confidence score (e.g., exceeding respective thresholds) are determined. Thus, for each abnormal tissue detection, a modal diagnosis confidence score and a modal anatomic location may be output, for example, to the monitor 316 for consideration by a radiologist making a diagnosis. Using the modal diagnosis confidence scores and a modal anatomic locations, the radiologist may approach the images in a more targeted and direct manner by review of the high confidence locations. Further, according to some example embodiments, the data fusion machine 312 may be configured to provide quantitative values for uncertainty with respect to the modal anatomic locations and also the location associations made when generating the modal correspondence anatomic model. These uncertainties may also be considered by the radiologist. Additionally, according to some example embodiments, to obtain feedback on the diagnosis results, a receiver operating characteristic (ROC) analysis may be performed and compared to a similar ROC analysis of a conventional approach.

Accordingly, based on the forgoing process, the UDF approach uses the cancer-likeness or modality likelihood scores in feature fusion to compute the probability that the detected abnormal tissue is malignant. A location is also provided with a quantified location uncertainty. Cancer detection may be determined when the probabilities of correct association and malignant abnormal tissue are sufficiently high. The radiologist may not only be provided a declared malignant abnormal tissue detection, but also an assessment by cognitive computing in terms of the probabilities of malignancy detection.

Figure 4:
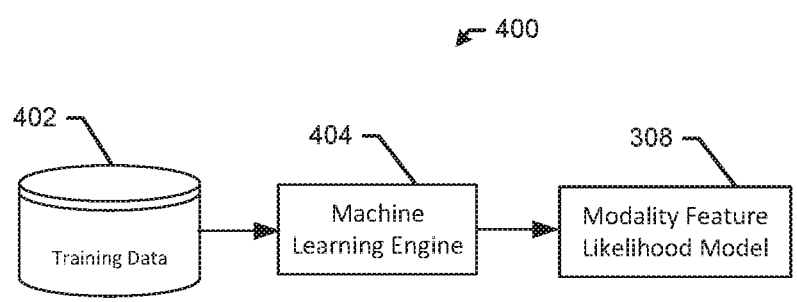
FIG. 4 illustrates an example system and method for generating a modality feature likelihood model according to some example embodiments.

As described above, the system 300, according to some example embodiments, leverages a modality feature likelihood model 308. FIG. 4 provides a system and method for generating the modality feature likelihood model 308. In this regard, a modality feature likelihood model may be generated for each modality and incorporated into the implementation as described above. To generate the modality feature likelihood model 308, an offline process may be utilized. However, according to some example embodiments, the modality feature likelihood model 308 may be updated as part of an online process.

Initially, training data 402 may be obtained that includes truth data for malignant and benign abnormal tissue that have been previously proven and validated via biopsy or the passage of time with or without a cancer diagnosis. As such, the training data 402 may be validated based on positive diagnosis and false-positive diagnosis performance. Image features, such as tissue texture, may be previously identified from, for example, radiologist knowledge to develop engineered features. Further deep learning methods may be used to discover features from the data. In other words, use deep learning may be used to discover features that may then be input to subsequent machine learning such as SVM. An example may be seen in Athiwaratkun, Ben and Keegan Kang, "Feature representation in convolutional neural networks," arXiv preprint arXiv: 1507.02313 (2015), the entire contents of which is herein incorporated by reference. The training data 402 may be evaluated by a machine learning engine 404, such as a Support Vector Machine (SVM), to construct models for statistical likelihood scores for malignant versus benign tissue. As described above, the resultant modality feature likelihood model 308 can be applied to data currently under evaluation for a diagnosis to provide quantitative cancer-likeness scores or modality likelihood scores. The machine learning engine 404 can therefore utilize machine learning techniques to compute a model for cancer-likeness scoring thereby providing a quantitative measure of how strongly cancer is indicated. In contrast to conventional methods that may only provide a binary malignancy/benign result as a machine learning decision, decision variables from machine learning may be used to form likelihoods. According to some example embodiments, the cancer-likeness score that can be determined using the modality feature likelihood model 308 can allow for leveraging the important upstream information that is lost when binary decision outputs are used instead of decision variables.

Figure 5:
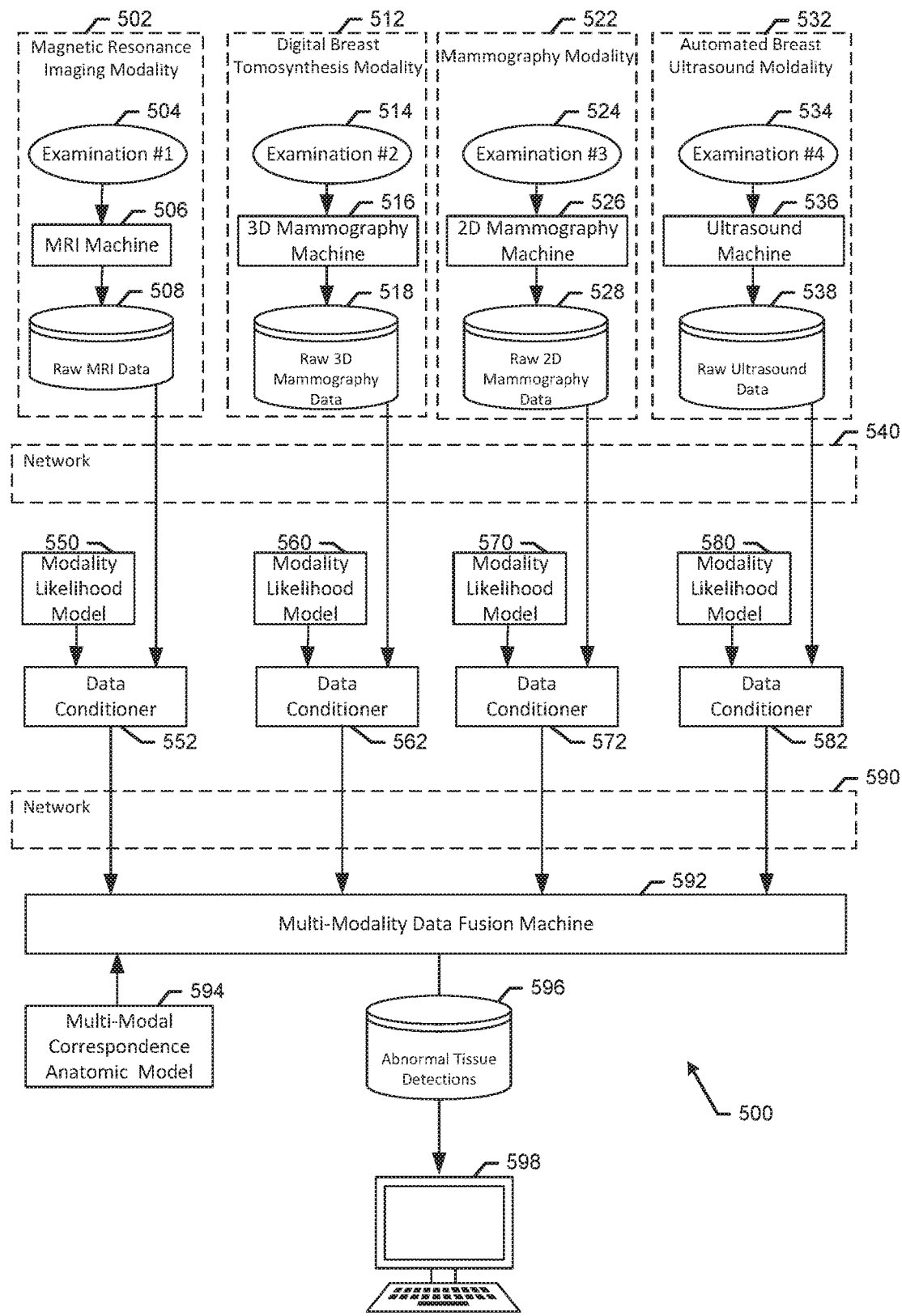
FIG. 5 illustrates a multi-modal system for generating abnormal tissue detections according to some example embodiments.

Now with reference to FIG. 5, a multi-modal system 500 configured to use UDF is provided. In this regard, the system 500 generally operates similar to the single modality system 300, with the exception that fusion is performed in an inter-modal manner. In this regard, the example multi-modal system 500 may be configured to consider any number of modalities and any number of instances of the same modality. Here, four different modalities are represented, i.e., MRI, DBT, mammography, and ABUS, that are applied in the context of the same body and area of interest.

Within the magnetic resonance imaging modality 502, an examination 504 may occur where an MRI machine 506 captures raw MRI data 508 to be used as MRI modality examination data. Within the digital breast tomosynthesis modality 512, an examination 514 may occur where a 3D mammography machine 516 captures raw 3D mammography data 518 to be used as DBT modality examination data. Within the mammography modality 522, an examination 524 may occur where a 2D mammography machine 526 captures raw 2D mammography data 528 to be used as mammography modality examination data. Finally, within the automated breast ultrasound modality 532, an examination 534 may occur where an ultrasound machine 536 captures raw ultrasound data 538 to be used as ultrasound modality examination data. In each instance, the modality examination data may be transmitted to a respective data conditioner 552, 562, 572, and 582, possibly via a network 540.

Each data conditioner 552, 562, 572, and 582 may be embodied and be configured to operate in the same or similar manner as the data conditioner 310 described above with respect to a particular modality. As such, the data conditioners 552, 562, 572, and 582 may be configured to determine a respective set of modality detection candidates based on the modality examination data and a respective modality feature likelihood model 550, 560, 570, and 580. In this regard, each data conditioner 552, 562, 572, and 582 may evaluate the data segments of the modality examination data (e.g., respective data 508, 518, 528, and 538) and determine the modality detection candidates, with each candidate comprising a modality likelihood score and a modality relative location.

The respective sets of modality detection candidates may be transmitted, possibly via a network 590, to the multi-modality data fusion machine 592 to perform data fusion on a multi-modal level. As such, the multi-modality data fusion machine 592 may be configured to generate a multi-modal correspondence anatomic model 594 of the area of interest by registering the modality examination data segments from all participating modalities 502, 512, 522, and 532. The approach for generating the multi-modal correspondence anatomic model 594 may be similar to how the modal correspondence anatomic model 313 is generated, albeit with respect to modality examination data segments from more than one modality. For example, in one embodiment, to facilitate performing the data fusion, a multi-modal correspondence anatomic model 594 is generated by the multi-modality data fusion machine 592. To generate the multi-modal correspondence anatomic model 594, each of the multi-modality examination data segments may be evaluated as part of a registration process to determine the spatial relationship of the multi-modality examination data segments to each other. The registration process may involve, for example, identifying mutual information amongst the data segments or data segment similarity measures, while accounting for tissue deformation such as breast compression for mammography. In an embodiment, the multi-modality data fusion machine 592 may be configured to analyze features within the multi-modality examination data segments to identify registration features and extract matchable characteristics of the registration features to locationally link the multi-modality examination data segments. In this regard, for example, the multi-modality data fusion machine 592 may be configured to evaluate each of the multi-modality examination data segments to identify registration features within the multi-modality examination data segments that exceed a characteristic threshold and include a matchable characteristic. For example, the characteristic threshold may be an image contrast threshold or a sharpness threshold, and a feature that exceeds such as characteristic threshold may be likely to have, for example, matchable characteristics such as sharp edges. Accordingly, the multi-modality data fusion machine 592 may be configured to identify, for a selected registration feature, two or more multi-modality examination data segments that include the matchable characteristic (e.g., the particular sharp edges). Upon identifying multi-modality examination data segments that include the matchable characteristic (or a predictable variation of the matchable characteristic based on relative known locational relationships between the modality examination segments), the multi-modality data fusion machine 592 generates a location-based linkage between the two or more multi-modality examination data segments associated with the selected registration feature for inclusion in the multi-modal correspondence anatomic model 594. As such, the multi-modal correspondence anatomic model 594 may take the form of, for example, a spline model, finite element elasticity model, or a machine learning spatial transformer network. Due to the inherent 3D nature of much of the multi-modality examination data 508, 518, 528, and 538, the registration process may use stacks of slices of multi-modality examination data as blocks of data to build a correspondence model within and between modalities. In this manner, mutual information and similarity measures may be used to register stacks of slices of multi-modality data simultaneously.

Further, the multi-modality data fusion machine 592, which may be embodied as specially configured processing circuitry, may be configured to make determinations for one or more abnormal tissue detections 596 by fusing the sets of modality detection candidates provided by each modality using the multi-modal correspondence anatomic model 594. Via the abnormal tissue detections 596 associated modal diagnosis confidence scores and multi-modal anatomic locations may be provided, for example, to the monitor 598 for consideration by a radiologist as described above. As such, the collection of data segments from a plurality of modalities may be considered in combination to achieve improved abnormal tissue detection results.

An example involving registration for different modalities may be found in, for example, Behrenbruch, Christian P. et al., "Mri—mammography 2d/3d data fusion for breast pathology assessment," In *International Conference on Medical Image Computing and Computer-Assisted Intervention*, pp. 307-316. Springer, Berlin, Heidelberg, 2000, the entire contents of which are hereby incorporated herein by reference.

A problem in the current state of the art exists as a variety of discrete medical imaging devices produce an abundance of imaging data in varying formats. Currently, no tools exist to manage the volume of data produced by the multiple imaging devices. The abundance of imaging data may lead to misdiagnosis such as false positives or a failure to detect an abnormality (e.g., cancerous tissue). In one embodiment, the invention described herein solves this problem by collecting data (e.g., upstream data) from the many different types of medical imaging devices (e.g., PET scans, ultrasound, x-rays, etc.) processing the voluminous image data and combining or fusing this data together to detect and present potential abnormalities that otherwise would have been misdiagnosed.

Figure 6:
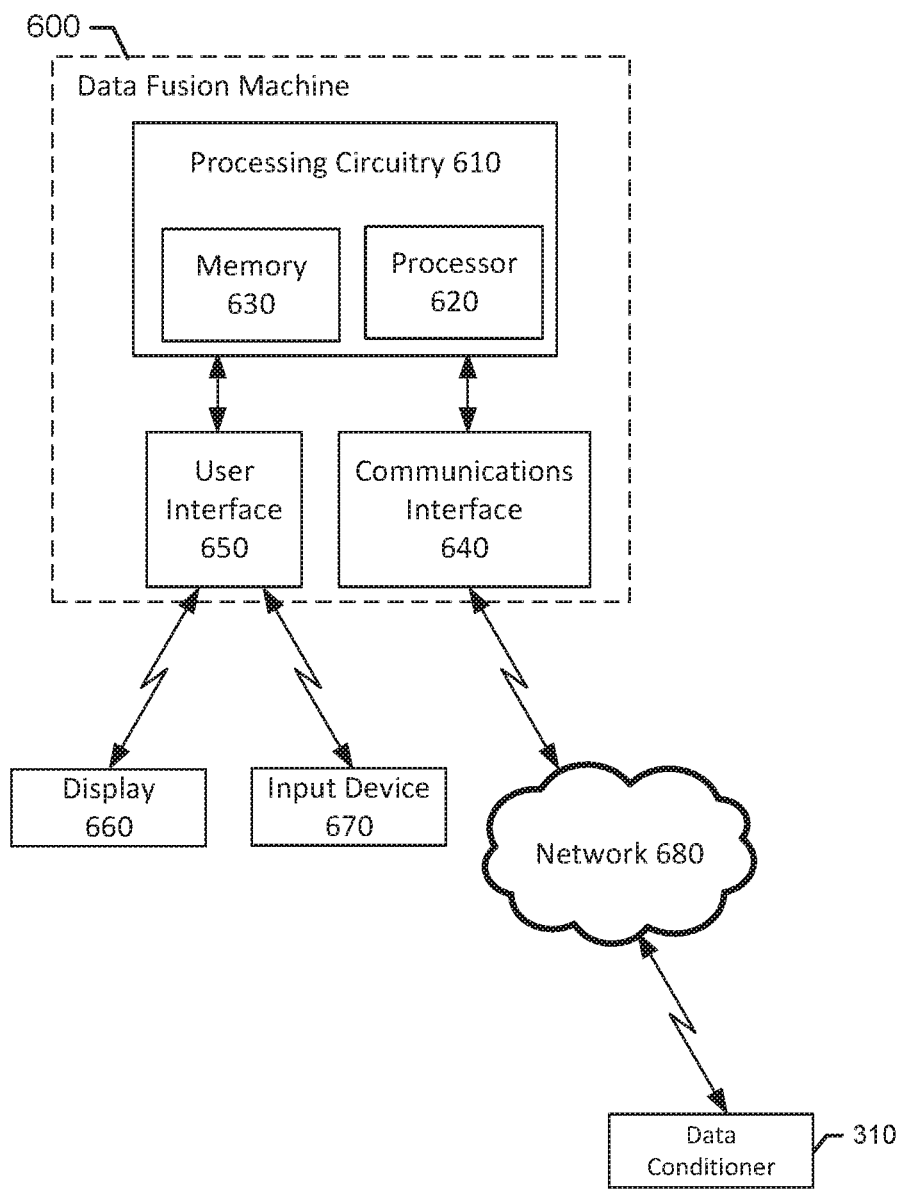
FIG. 6 illustrates a conceptual block diagram of an apparatus for generating abnormal tissue detections according to some example embodiments.

FIG. 6 provides a block diagram of an example of an apparatus 600 configured to operate as a data fusion machine in accordance with the operation of the data fusion machine 312 or the multi-modality data fusion machine 592, according to some example embodiments. The apparatus 600 may include components configured to determine modal abnormal tissue detections by fusing modality detection candidates using the modal correspondence anatomic model, and provide modal diagnosis confidence scores and modal anatomic locations based on respective modal abnormal tissue detections.

In this regard, the apparatus 600 may comprise processing circuitry 610 that may be in operative communication with or embody a communications interface 640 and a user interface 650. The processing circuitry 610 may interact with or embody a memory 630 and a processor 620. The processing circuitry 610 may be configurable to perform operations described herein. In this regard, the processing circuitry 610 may be configured to perform data fusion operations according to an example embodiment. In some embodiments, the processing circuitry 610 may be embodied as a chip or chip set. In other words, the processing circuitry 610 may comprise one or more physical packages (e.g., chips) including materials, components or wires on a structural assembly (e.g., a baseboard). The processing circuitry 610 may be configured to receive inputs (e.g., via peripheral components such as user interface 650, communications interface 640, and including the memory 630), perform actions based on the inputs, and generate outputs (e.g., for provision to peripheral components). In an example embodiment, the processing circuitry 610 may include one or more instances of a processor 620, associated circuitry, and memory 630. As such, the processing circuitry 610 may be embodied as a circuit chip (e.g., an integrated circuit chip, such as a field programmable gate array (FPGA) or a Graphics Processing Unit (GPU)) configured (e.g., with hardware, software or a combination of hardware and software) to perform operations described herein.

In an example embodiment, the memory 630 may include one or more non-transitory memory devices such as, for example, volatile or non-volatile memory that may be either fixed or removable. The memory 630 may be configured to store information, data in a database, applications, instructions or the like for enabling, for example, object recognition and presentation and to carry out various functions in accordance with example embodiments. For example, the memory 630 could be configured to buffer input data for processing by the processing circuitry 610. Additionally or alternatively, the memory 630 could be configured to store instructions for execution by the processing circuitry 610. Among the contents of the memory 630, applications may be stored for execution by the processing circuitry 610 in order to carry out the functionality associated with each respective application.

As mentioned above, the processing circuitry 610 may be embodied in a number of different ways. For example, the processing circuitry 610 may be embodied as various processing means such as one or more processors 620 that may be in the form of a microprocessor or other processing element, a coprocessor, a controller or various other computing or processing devices including integrated circuits such as, for example, an ASIC (application specific integrated circuit), an FPGA, or the like. In an example embodiment, the processing circuitry 610 may be configured to execute instructions stored in the memory 630 or otherwise accessible to the processing circuitry 610. As such, whether configured by hardware or by a combination of hardware and software, the processing circuitry 610 may represent an entity (e.g., physically embodied in circuitry—in the form of processing circuitry 610) capable of performing operations according to example embodiments while configured accordingly. Thus, for example, when the processing circuitry 610 is embodied as an ASIC, FPGA, or the like, the processing circuitry 610 may be specifically configured hardware for conducting the operations described herein. Alternatively, as another example, when the processing circuitry 610 is embodied as an executor of software instructions, the instructions may specifically configure the processing circuitry 610 to perform the operations described herein.

The communication interface 640 may include one or more interface mechanisms for enabling communication with other devices external to apparatus 600, via, for example, a network 680, such as a local area network. In some cases, the communication interface 640 may be any means such as a device or circuitry embodied in either hardware, or a combination of hardware and software that is configured to receive or transmit data from/to devices in communication with the processing circuitry 610. The communications interface 640 may be a wired or wireless interface and may support various communications protocols. As shown in FIG. 6, the apparatus 600 may be in operable communication with, for example, the data conditioner 310 via the network 680.

The user interface 650 may be controlled by the processing circuitry 610 to interact with a user. In this regard, via the user interface 650, the processing circuitry 610 may be configured to output to a user via an output device such as, for example, driving a display 660 and receive input from a user via an input device 670 such as, for example, audio input, which may be, for example, a microphone. The user interface 650 may also produce outputs, for example, via audio output, which may be for example, a speaker. According to some example embodiments, the user interface may also operably couple to other user input devices such as, for example, a keyboard, mouse, touch screen, or the like.

In an example embodiment, the processing circuitry 610 may be embodied as, include or otherwise control, the apparatus 600 to perform various operations associated with detecting abnormal tissue as described herein. As such, in some embodiments, the processing circuitry 610 may be said to cause each of the operations described in connection with, for example, the techniques described with respect data fusion machine 312, the data conditioner 310, the machine learning engine 404, the data conditioners 552, 562, 572, and 582, and/or multi-modality data fusion machine 592. Further, the processing circuitry 710 may also be configured to cause each of the operations described in connection with the example methods described in association with FIGS. 7 and 8. In this regard, the processing circuitry 610 may therefore undertake the corresponding functionalities responsive to execution of instructions or algorithms configuring the processing circuitry 610 accordingly. The processing circuitry 610 may provide programmable control signals, selections, and the like to control the operation of the apparatus 600 responsive to execution of instructions stored in the memory 630.

Figure 7:
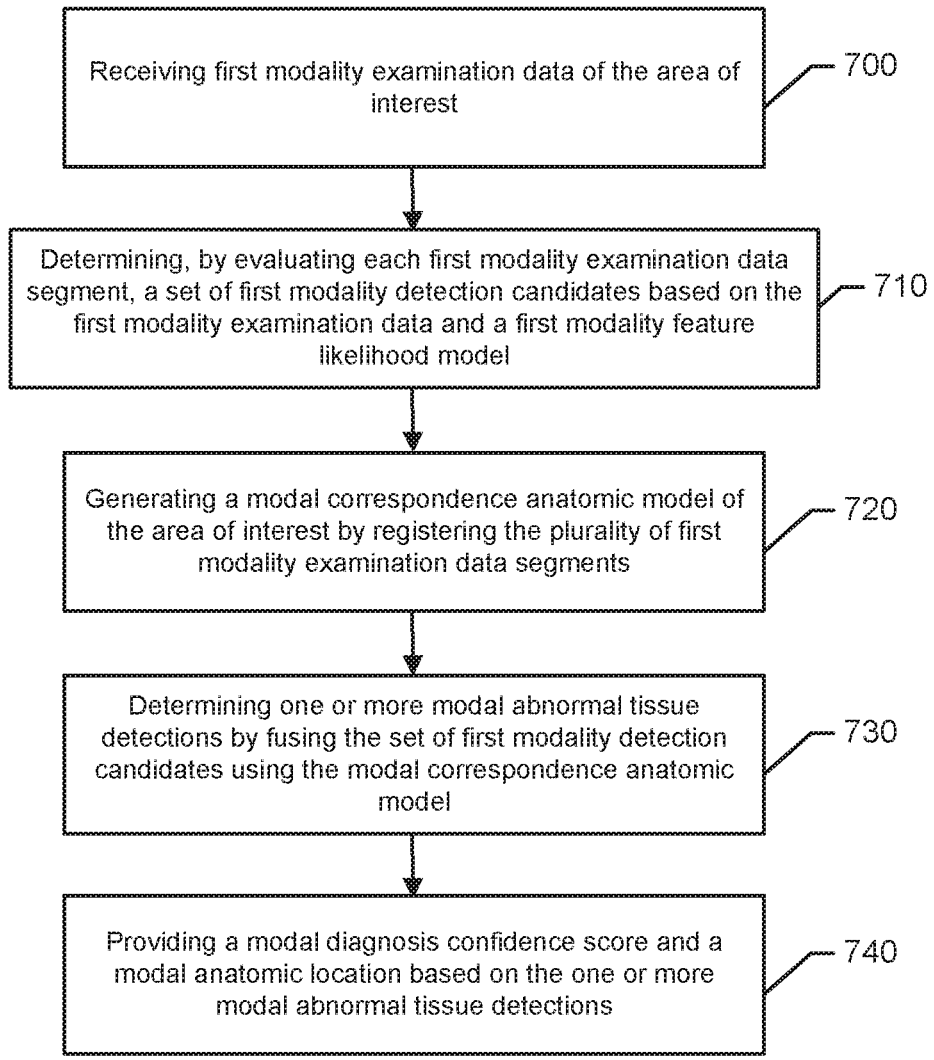
FIG. 7 illustrates a flowchart of an example method for generating abnormal tissue detections based on a single modality according to an example embodiment.

FIG. 7 provides a flowchart of an example method for characterizing and locating abnormal tissue in an area of interest in a body based on data originating from a single modality according to some example embodiments. In this regard, the example method comprises receiving first modality examination data of the area of interest at 700. The first modality examination data may have been captured by a medical imaging device, such as modality sensor 304. The first modality examination data may comprise a plurality of first modality examination data segments. Each first modality examination data segment may be associated with a portion of the area of interest or a first modality sensor field of view into the area of interest.

The example method may also include, at 710, determining, by evaluating each first modality examination data segment, a set of first modality detection candidates based on the first modality examination data and a first modality feature likelihood model. In this regard, each first modality detection candidate may comprise a first modality likelihood score and a first modality relative location. The set of first modality detection candidates may be determined by a data conditioner (e.g., data conditioner 310) using a data conditioner computing machine. Additionally, at 720, the example method may include generating, by a data fusion machine (e.g., data fusion machine 312), a modal correspondence anatomic model of the area of interest by registering the plurality of first modality examination data segments. At 730, the example method may include determining, by a data fusion machine (e.g., data fusion machine 312), one or more modal abnormal tissue detections by fusing the set of first modality detection candidates using the modal correspondence anatomic model. Additionally, at 740, the example method may also include providing, by a data fusion machine (e.g., data fusion machine 312), a modal diagnosis confidence score and a modal anatomic location based on the one or more modal abnormal tissue detections.

Figure 8:
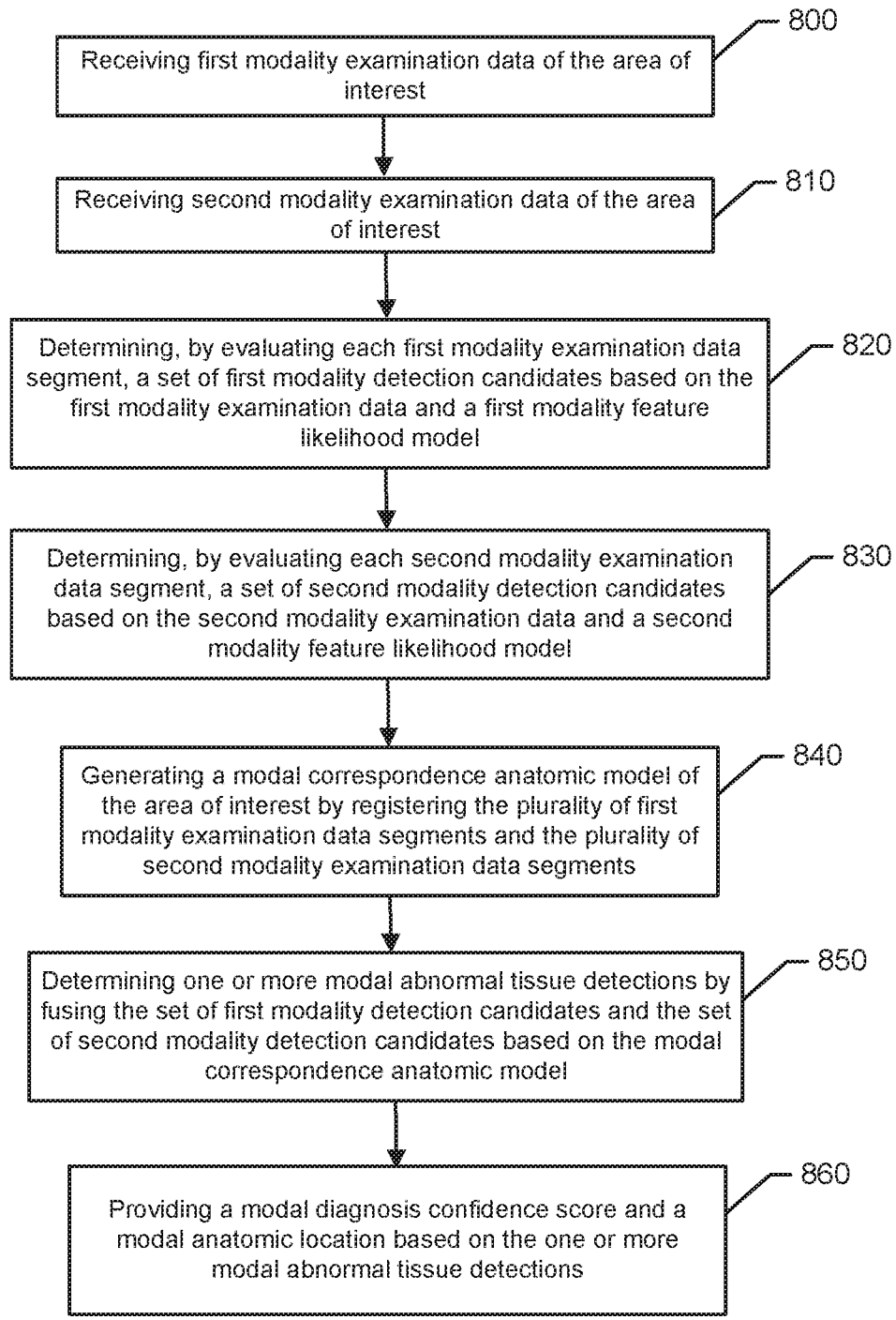
FIG. 8 illustrates a flowchart of an example method for generating abnormal tissue detections based on multiple modalities according to an example embodiment.

FIG. 8 provides a flowchart of another example method for characterizing and locating abnormal tissue in an area of interest in a body based on data originating from two or more modalities according to some example embodiments. In this regard, the example method comprises receiving first modality examination data of the area of interest at 800. The first modality examination data may have been captured by a medical imaging device, such as modality sensor 304, MRI machine 506, 3D mammography machine 516, 2D mammography machine 526, ultrasound machine 536, or the like. In this regard, the first modality examination data may comprise a plurality of first modality examination data segments. Each first modality examination data segment may be associated with a portion of the area of interest or a first modality sensor field of view into the area of interest. Additionally, the example method may include receiving second modality examination data of the area of interest at 810. The second modality examination data may have been captured by a medical imaging device, such as modality sensor 304, MRI machine 506, 3D mammography machine 516, 2D mammography machine 526, ultrasound machine 536, or the like. Similarly, the second modality examination data may comprise a plurality of second modality examination data segments. Each second modality examination data segment may be associated with a portion of the area of interest or a second modality sensor field of view into the area of interest.

The example method may also include, at 820, determining, by evaluating each first modality examination data segment, a set of first modality detection candidates based on the first modality examination data and a first modality feature likelihood model. The set of first modality detection candidates may be determined by a data conditioner (e.g., one of data conditioners 310, 552, 562, 572, or 582) using data conditioner computing machines. In this regard, each first modality detection candidate may comprise a first modality likelihood score and a first modality relative location. Similarly, at 830, determining, by evaluating each second modality examination data segment, a set of second modality detection candidates based on the second modality examination data and a second modality feature likelihood model. The set of second modality detection candidates may be determined by a data conditioner (e.g., one of data conditioners 310, 552, 562, 572, or 582) using data conditioner computing machines. In this regard, each second modality detection candidate comprises a second modality likelihood score and a second modality relative location.

Additionally, at 840, the example method may include generating, by a data fusion machine (e.g., multi-modal data fusion machine 592), a modal correspondence anatomic model of the area of interest by registering the plurality of first modality examination data segments and the plurality of second modality examination data segments. At 850, the example method may include determining, by a data fusion machine (e.g., multi-modal data fusion machine 592), one or more modal abnormal tissue detections by fusing the set of first modality detection candidates and the set of second modality detection candidates based on the modal correspondence anatomic model. Additionally, at 860, the example method may also include providing, by a data fusion machine (e.g., multi-modal data fusion machine 592), a modal diagnosis confidence score and a modal anatomic location based on the one or more modal abnormal tissue detections.

The example methods provided herein and those described with respect to FIGS. 7 and 8 may be further modified in a variety of ways. For example, example methods may further comprise generating, via machine learning, the first modality likelihood model based on first modality examination training data that has been validated based on positive diagnosis and false-positive diagnosis performance. Additionally, according to some example embodiments, the example methods may include generating, via machine learning, the second modality likelihood model based on second modality examination training data that has been validated based on positive diagnosis and false-positive diagnosis performance. Further, according to some example embodiments, the modal diagnosis confidence score may indicate a probability that abnormal tissue located at the modal anatomic location is malignant. Additionally, the first modality likelihood scores and the second modality likelihood scores may be non-binary, quantitative cancer-likeness scores. According to some example embodiments, the first modality examination data may comprise first image data captured by a first modality sensor, and the second modality examination data may comprise second image data captured by a second modality sensor. Each first modality examination data segment or each second modality examination data segment may be associated with two-dimensional, cross-section images of the area of interest.

Additionally, determining the set of first modality detection candidates may comprise determining the set of first modality detection candidates by evaluating each first modality examination data segment in isolation from the other first modality examination data segments. Similarly, determining the set of second modality detection candidates may comprise determining the set of second modality detection candidates by evaluating each second modality examination data segment in isolation from the other second modality examination data segments and first modality examination data segments. According to some example embodiments, example methods may include associating features and location data between the first modality examination data segments using statistical data association. According to some example embodiments, example methods may include associating features and location data between the first modality examination data segments and the second modality examination data segments using statistical data association. Additionally, some example methods may include determining, based on associated features and location data, which first modality detection candidates correspond to a same abnormal tissue with a probability of correct association. Further, some example methods may include determining, based on associated features and location data, which first modality detection candidates and which second modality detection candidates correspond to a same abnormal tissue with a probability of correct association. Additionally, according to some example embodiments, the first modality examination data or the second modality examination data may be captured by a sensor configured to operate based on at least one of: ultrasound, positron emission tomography (PET), computed tomography (CT), x-rays, magnetic resonance imaging (MRI), or single-photon emission computed tomography (SPECT) during a first examination of the body.

Additionally, according to some example embodiments, fusing the set of first modality detection candidates may include generating a plurality of object association hypotheses, where each object association hypothesis is associated with one or more modality detection candidates based at least on the first modality relative locations. Further, fusing may include determining a probability of association for each object association hypothesis, removing one or more object association hypotheses based on the probability of association for the object association hypothesis failing to meet an association threshold, and determining the one or more modal abnormal tissue detections based on the remaining object association hypotheses.

According to some example embodiments, registering the plurality of first modality examination data segments may include evaluating, by the data fusion machine, each of the modality examination data segments to identify registration features within the modality examination data segments that exceed a characteristic threshold and include a matchable characteristic. Further, registering may include identifying, for a selected registration feature, two or more modality examination data segments that include the matchable characteristic, and generating a location-based linkage between the two or more modality examination data segments associated with the selected registration feature for inclusion in the modal correspondence anatomic model.

The following publications are herein incorporated by reference in their entirety: (1) Teare P. et al., "Malignancy Detection on Mammography Using Dual Deep Convolutional Neural Networks and Genetically Discovered False Color Input Enhancement," Journal of Digital Imaging, 2017 Aug. 30(4):499-505; (2) Trister A D. et al., "Will machine learning tip the balance in breast cancer screening?," JAMA oncology, 2017 Nov. 3(11):1463-4; (3) Geras K J. et al., "High-resolution breast cancer screening with multi-view deep convolutional neural networks," arXiv preprint arXiv:1703.07047, 2017 March, 21; (4) Shi X et al., "Detection and classification of masses in breast ultrasound images," Digital Signal Processing, 2010 May, 20(3):824-36; (5) Amit G. et al., "Classification of breast MRI lesions using small-size training sets: comparison of deep learning approaches," InMedical Imaging 2017: Computer-Aided Diagnosis 2017 March, (Vol. 10134, p. 101341H), International Society for Optics and Photonics; (6) Arevalo J. et al, "Representation learning for mammography mass lesion classification with convolutional neural networks," Computer methods and programs in biomedicine, 2016 April, 127:248-57; and (7) Newman, Andrew J. et al., "Upstream data fusion: History, technical overview, and applications to critical challenges," Johns Hopkins APL technical digest 31.3 (2013): 215-233.

Many modifications and other embodiments set forth herein will come to mind to one skilled in the art to which these inventions pertain having the benefit of the teachings presented in the foregoing descriptions and the associated drawings. Therefore, it is to be understood that the embodiments are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A method for characterizing and locating abnormal tissue in an area of interest in a body, the method comprising:
   receiving first modality examination data of the area of interest captured by a medical imaging device, the first modality examination data comprising a plurality of first modality examination data segments, each first modality examination data segment being associated with a portion of the area of interest or a first modality sensor field of view into the area of interest;
   determining, by evaluating each first modality examination data segment with a computing machine, a set of first modality detection candidates based on the first modality examination data and a first modality feature likelihood model, each first modality detection candidate comprising a first modality likelihood score and a first modality relative location;
   generating, by a data fusion machine, a modal correspondence anatomic model of the area of interest by registering the plurality of first modality examination data segments;
   determining, by the data fusion machine, one or more modal abnormal tissue detections by fusing the set of first modality detection candidates using the modal correspondence anatomic model; and
   providing, by the data fusion machine, a modal diagnosis confidence score and a modal anatomic location based on the one or more modal abnormal tissue detections.

2. The method of claim 1 further comprising:
   receiving second modality examination data of the area of interest captured by a second medical imaging device, the second modality examination data comprising a plurality of second modality examination data segments, each second modality examination data segment being associated with a portion of the area of interest or a second modality sensor field of view into the area of interest; and
   determining, by evaluating each second modality examination data segment, a set of second modality detection candidates based on the second modality examination data and a second modality feature likelihood model, each second modality detection candidate comprising a second modality likelihood score and a second modality relative location;
   wherein generating the modal correspondence anatomic model comprises registering the plurality of first modality examination data segments and the plurality of second modality examination data segments;
   wherein determining the one or more modal abnormal tissue detections comprises fusing the set of first modality detection candidates and the set of second modality detection candidates based on the modal correspondence anatomic model.

3. The method claim 1, wherein fusing the set of first modality detection candidates comprises:
   generating, by the data fusion machine, a plurality of object association hypotheses, each object association hypothesis being associated with one or more modality detection candidates based at least on the first modality relative locations;
   determining a probability of association for each object association hypothesis;
   removing one or more object association hypotheses based on the probability of association for the object association hypothesis failing to meet an association threshold; and
   determining, by the data fusion machine, the one or more modal abnormal tissue detections based on the remaining object association hypotheses.

4. The method of claim 1, wherein registering the plurality of first modality examination data segments comprises:
   evaluating, by the data fusion machine, each of the modality examination data segments to identify registration features within the modality examination data segments that exceed a characteristic threshold and include a matchable characteristic;
   identifying, for a selected registration feature, two or more modality examination data segments that include the matchable characteristic; and
   generating a location-based linkage between the two or more modality examination data segments associated with the selected registration feature for inclusion in the modal correspondence anatomic model.

5. The method of claim 1, further comprising generating, via machine learning, the first modality likelihood model based on first modality examination training data that has been validated based on positive diagnosis and false-positive diagnosis performance.

6. The method of claim 1, wherein the modal diagnosis confidence score indicates a probability that abnormal tissue located at the modal anatomic location is malignant.

7. The method of claim 1, wherein the first modality likelihood scores are non-binary, quantitative cancer-likeness scores.

8. The method of claim 1, wherein each first modality examination data segment is associated with a two-dimensional, cross-section images of the area of interest.

9. The method of claim 1, further comprising:
   associating features and location data between the first modality examination data segments using statistical data association; and determining, based on associated features and location data, which first modality detection candidates correspond to a same abnormal tissue with a probability of correct association.

10. The method of claim 1, wherein the medical imaging device is at least one of: ultrasound, positron emission tomography (PET), computed tomography (CT), x-rays, magnetic resonance imaging (MRI), or single-photon emission computed tomography (SPECT) during a first examination of the body.

11. A system for characterizing and locating abnormal tissue in an area of interest in a body, the system comprising processing circuitry configured to:
receive first modality examination data of the area of interest, the first modality examination data comprising a plurality of first modality examination data segments, each first modality examination data segment being associated with a portion of the area of interest or a first modality sensor field of view into the area of interest;
determine, by evaluating each first modality examination data segment, a set of first modality detection candidates based on the first modality examination data and a first modality feature likelihood model, each first modality detection candidate comprising a first modality likelihood score and a first modality relative location;
generate a modal correspondence anatomic model of the area of interest by registering the plurality of first modality examination data segments;
determine one or more modal abnormal tissue detections by fusing the set of first modality detection candidates using the modal correspondence anatomic model; and
provide a modal diagnosis confidence score and a modal anatomic location based on the one or more modal abnormal tissue detections.

12. The system of claim 11, wherein the processing circuitry is further configured to:
receive second modality examination data of the area of interest, the second modality examination data comprising a plurality of second modality examination data segments, each second modality examination data segment being associated with a portion of the area of interest or a second modality sensor field of view into the area of interest; and
determine, by evaluating each second modality examination data segment, a set of second modality detection candidates based on the second modality examination data and a second modality feature likelihood model, each second modality detection candidate comprising a second modality likelihood score and a second modality relative location;
wherein being configured to generate the modal correspondence anatomic model comprises being configured to register the plurality of first modality examination data segments and the plurality of second modality examination data segments;
wherein being configured to determine the one or more modal abnormal tissue detections comprises being configured to fuse the set of first modality detection candidates and the set of second modality detection candidates based on the modal correspondence anatomic model.

13. The system of claim 11, wherein the processing circuitry configured to fuse the set of first modality detection candidates, includes being configured to:
generate a plurality of object association hypotheses, each object association hypothesis being associated with one or more modality detection candidates based at least on the first modality relative locations;
determine a probability of association for each object association hypothesis;
remove one or more object association hypotheses based on the probability of association for the object association hypothesis failing to meet an association threshold; and
determine the one or more modal abnormal tissue detections based on the remaining object association hypotheses.

14. The system of claim 11, wherein the processing circuitry configured to register the plurality of first modality examination data segments includes being configured to:
evaluate, by the data fusion machine, each of the modality examination data segments to identify registration features within the modality examination data segments that exceed a characteristic threshold and include a matchable characteristic;
identify, for a selected registration feature, two or more modality examination data segments that include the matchable characteristic; and
generate a location-based linkage between the two or more modality examination data segments associated with the selected registration feature for inclusion in the modal correspondence anatomic model.

15. The system of claim 11, wherein the processing circuitry is further configured to generate, via machine learning, the first modality likelihood model based on first modality examination training data that has been validated based on positive diagnosis and false-positive diagnosis performance.

16. The system of claim 11, wherein the modal diagnosis confidence score indicates a probability that abnormal tissue located at the modal anatomic location is malignant.

17. The system of claim 11, wherein the first modality likelihood scores are non-binary, quantitative cancer-likeness scores.

18. The system of claim 11, wherein the processing circuitry is configured to determine the set of first modality detection candidates by evaluating each first modality examination data segment in isolation from the other first modality examination data segments.

19. The system of claim 11, wherein the processing circuitry is further configured to:
associate features and location data between the first modality examination data segments using statistical data association; and
determine, based on associated features and location data, which first modality detection candidates correspond to a same abnormal tissue with a probability of correct association.

20. The system of claim 11, wherein the first modality examination data is captured by at least one of: ultrasound, positron emission tomography (PET), computed tomography (CT), x-rays, magnetic resonance imaging (MRI), or single-photon emission computed tomography (SPECT) during a first examination of the body.

* * * * *